United States Patent [19]

Epstein

[11] Patent Number: 5,350,388
[45] Date of Patent: Sep. 27, 1994

[54] HEMOSTASIS APPARATUS AND METHOD

[75] Inventor: Adam Epstein, Brooklyn, N.Y.

[73] Assignee: Albert Einstein College of Medicine of Yeshiva University, Bronx, N.Y.

[21] Appl. No.: 893,109

[22] Filed: Jun. 3, 1992

Related U.S. Application Data

[60] Division of Ser. No. 708,101, May 28, 1991, Pat. No. 5,186,711, which is a continuation of Ser. No. 320,016, Mar. 7, 1989, abandoned.

[51] Int. Cl.$^5$ .............................................. A61F 2/00
[52] U.S. Cl. .................................. 606/154; 606/151; 600/37
[58] Field of Search ............... 606/151, 152, 153, 154; 623/11, 12; 600/37

[56] References Cited

U.S. PATENT DOCUMENTS

| | | | |
|---|---|---|---|
| 3,463,158 | 8/1969 | Schmitt et al. | 606/154 |
| 3,833,002 | 9/1974 | Palma | 606/154 X |
| 5,057,117 | 10/1991 | Atweh | 600/37 X |
| 5,059,211 | 10/1991 | Stack et al. | 606/154 X |
| 5,061,281 | 10/1991 | Mares et al. | 623/12 X |
| 5,171,262 | 12/1992 | MacGregor | 623/12 X |
| 5,236,447 | 8/1993 | Kubo et al. | 623/12 X |

OTHER PUBLICATIONS

Aglietti et al., "Traumatic Lesions of the Liver", Translation in U.S. 07/708,101.

Primary Examiner—Sam Rimell
Attorney, Agent, or Firm—Amster, Rothstein & Ebenstein

[57] ABSTRACT

A kit for effecting hemostatis of an organ comprises a mesh and a sack. The mesh is formed of semirigid, bioabsorbable material adapted to be generally conformingly disposed on at least the bleeding surface of an organ. The sack is made of flexible, elastic, air-impermeable material adapted to be elastically stretched over the mesh and over a substantial portion of the organ and then released to compress the organ portion and thereby decrease the flow of blood thereto. The sack further permits operative attachment of the undersurface thereof to a vacuum source so that portions of the organ may be pulled outwardly by the vacuum into the interstices of the underlying mesh to promote hemostasis.

14 Claims, 5 Drawing Sheets

FIG. 1
FIG. 1A
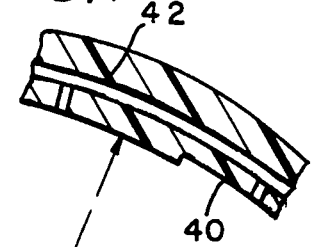
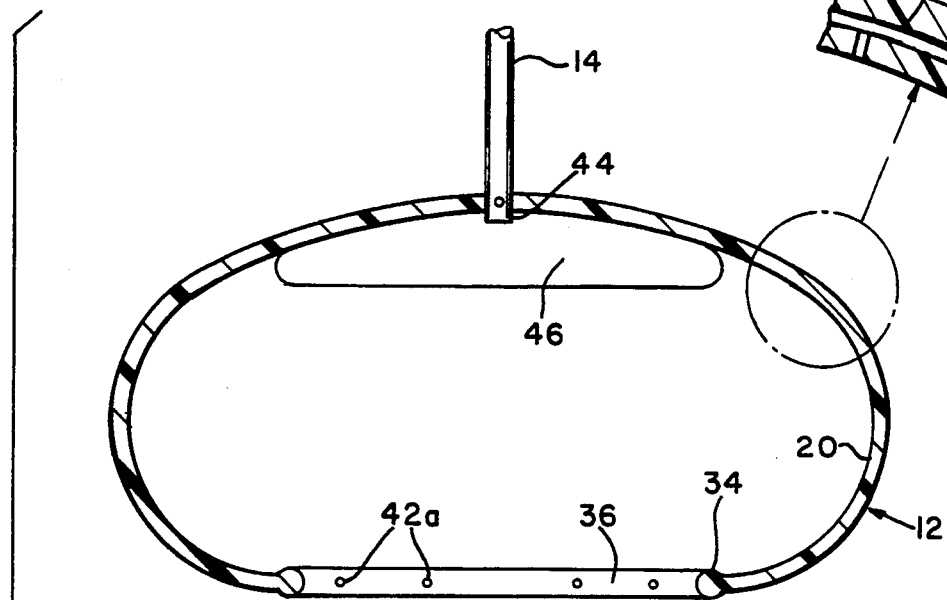
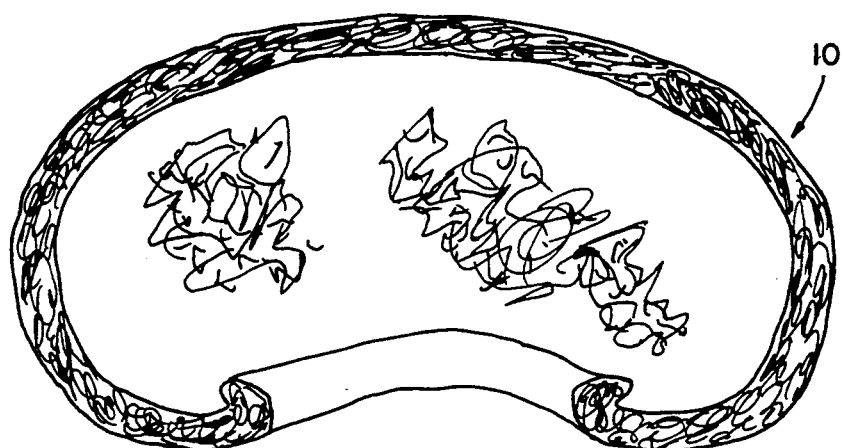
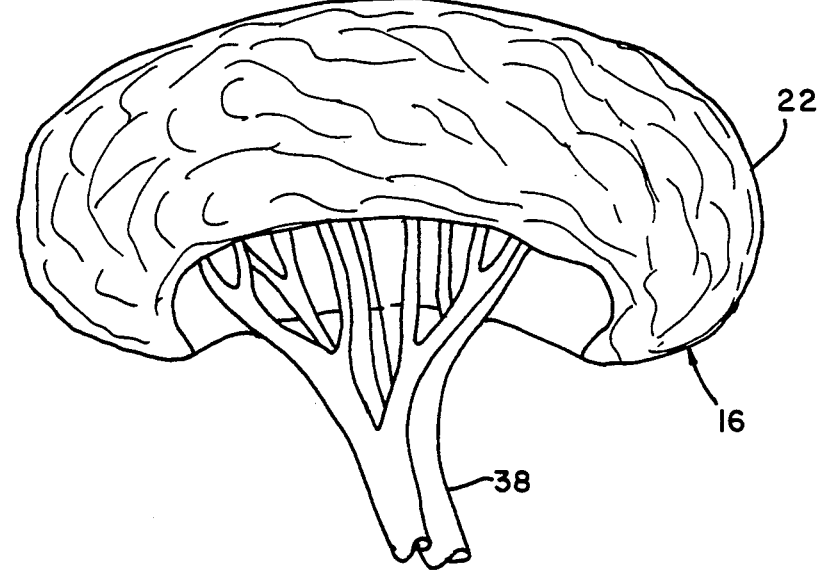

HEMOSTASIS APPARATUS AND METHOD

This is a divisional of copending application Ser. No. 07/708,101 filed on May 28, 1991, and now U.S. Pat. No. 5,186,711 itself a continuation of Ser. No. 07/320,016 filed on Mar. 7, 1989, now abandoned.

BACKGROUND OF THE INVENTION

The present invention relates to apparatus and methods for effecting hemostasis in an organ and, more particularly, to such apparatus and method useful in effecting hemostasis in a parenchymal organ such as the spleen or liver.

In an article entitled in English "Treatment Of Lesions of Parenchymatous Organs—Original Technique" originally published in Italy in 1986 under the title "Trattamento Delle Lesioni Degli Organi Parenchimatosi—Technica Originale" *Relazione 87° Congr. della Societa Italiana di Chirurgia—Torino* 1986 and abstracted in the Italian language publication *Journal of Surgery*, Vol. VII, No. 3 (March, 1986), Aglietti et al. disclose a technique for effecting hemostasis in a parenchymal organ such as the liver. The disclosed technique involves the use of a bioabsorbable, flat, single layer mesh which is manually conformed to the bleeding surface of the liver and a suction-applying cup which is placed over the mesh and the bleeding surface and manually maintained there until homorrhaging terminates.

The Agletti mesh is formed of a bioabsorbable material such as chromic catgut and is provided in rectangles or other shapes approximately 5×10 cm in area. The mesh is woven in a plain "left and right" weave and is therefore a flat monolayer. Typically each square centimeter utilizes about 10 cm of thread and is 4–5 millimeter thick, each interstice of the mesh being about 2 mm$^2$. The mesh provides a matrix of openings or interstices through which portions or fingers of the bleeding surface may be pulled, with the resulting infiltrating liver fingers being aligned generally parallel to one another. The suction, vacuum or negative pressure applied by the cup causes the parenchymal tissue to infiltrate the interstices or openings of the gridlike weave of he mesh. As soon as hemostasis is achieved, the cup is removed from the mesh and the previously bleeding surface, with the mesh being left imbedded in the parenchymal organ. In practice the Aglietti technique has not proven to be entirely satisfactory.

An important disadvantage of the Aglietti technique is the time that must be wasted while the surgeon holds the suction cup over the mesh of the bleeding surface until achievement of hemostasis. The normally strong blood flow to the parenchymal organ supports and extends hemorrhaging at bleeding surface by feeding additional blood to that surface. Further, as the cup must be held in place by the surgeon or his assistants until bleeding of the surface has been effectively terminated (as evidenced by the end of blood flow out of the cup), precious minutes may be wasted during which the surgeon's attention might be profitably directed elsewhere, especially where the trauma to the liver also affected other organs. In some instances complete hemostasis is not achieved for hours, and thus the patient must be left on the operating table for a prolonged period of time.

A further disadvantage of the Aglietti technique is that the portions of the parenchymal organ which infiltrate the interstices of the mesh are in a parallel orientation to one another. While the portions which have infiltrated and passed through to the other side of the mesh typically expand and join to some degree on such other side of the mesh, thereby promoting healing of the organ, there is no positive mechanical influence biasing such portions together so as to positively promote healing.

Accordingly, it is an object of the present invention to provide apparatus which accelerates the effecting of hemostasis by decreasing the blood flow to the organ being treated.

Another object is to provide such apparatus which positively promotes the joinder of the organ portions infiltrating the mesh.

A further object is to provide such apparatus which reduces or eliminates the time during which the surgeon must manually maintain the suction cup over the mesh on the bleeding surface.

It is also an object of the present invention to provide such apparatus which, in one embodiment, permits the incision to be closed and the patient removed from the operating table while suction is still being applied to the bleeding surface and mesh.

It is another object to provide a method of using such apparatus.

SUMMARY OF THE INVENTION

It has now been found that the above and related objects of the present invention are obtained by a device for effecting hemostasis of the bleeding surface of an organ, especially a parenchymal organ such as the spleen. The device contains a mesh and a sack. The mesh is formed of semirigid, bioabsorbable material adapted to be generally conformingly disposed on at least the bleeding surface of the organ. The sack is made of flexible, elastic, air-impermeable material configured and dimensioned to be elastically stretched over the mesh and over a substantial portion of the organ and, upon release, to compress the organ portion and thereby decrease the flow of blood thereto. The sack further includes means for operative attachment of the undersurface (i.e., inner surface) thereof to a vacuum source, so that portions of the organ may be pulled outwardly by the vacuum into the interstices of the underlying mesh to promote hemostasis.

In a preferred embodiment, the mesh is made of a semirigid material which is sufficiently rigid to preclude deformation under the vacuum created by the vacuum source but sufficiently flexible to be substantially conformed over the bleeding surface of the organ by the sack. The mesh contains a plurality of interlocked layers, at least some of one interstices of one layer being partially offset from the interstices of an adjacent layer, whereby some portions of the organ pulled outwardly by the vacuum into the interstices of the mesh are also pulled at an angle to the thickness of the mesh, thereby to promote joinder of some adjacent portions. Such a mesh may have a rice point knit. The mesh may be substantially coextensive with the sack, and preferably the sack and the mesh are both bioabsorbable and joined together as outer and inner layers, respectively, of a composite sack/mesh.

The sack, which may be made of bioabsorbable or non-bioabsorbable, material is adapted to be elastically stretched and then released to conform said mesh to the bleeding surface of the organ Upon release, the sack effects an at least partially operative seal with the organ about the bleeding surface thereof. The sack is made of an elastic material which is sufficiently elastic to reduce the size of the organ and thereby create a back pressure reducing or terminating blood flow thereinto and to generally conform the mesh to the outer surface of the organ.

The method of the present invention comprises the steps of applying a mesh of semirigid bioabsorbable material to at least the bleeding surface of an organ in generally conformingly disposition. Next a sack made of flexible, elastic, air-impermeable material is elastically stretched over the mesh and over a substantial portion of the organ, and then the sack is released to compress the organ portion and thereby decrease the flow of blood thereto. A vacuum is then applied to the undersurface of the sack to pull portions of the organ into the interstices of the underlying mesh to promote hemostasis.

The present invention further encompasses the combination of a mesh, a sack, a vacuum source, and means operatively attaching the vacuum source and the sack so that portions of an organ are pulled outwardly by the vacuum into the interstices of the underlying mesh to promote hemostasis. The sack and the mesh are both bioabsorbable and joined together as outer and inner layers, respectively, of a composite sack/mesh so that the mesh and sack are applied together as a unit to the organ. Preferably the vacuum source is disposed outside of the body containing the organ, the combination additionally including means for releasably securing the attaching means and the sack, the releasable securing means being releasable from outside the body.

The invention finally encompasses mesh for use in effecting hemostasis of an organ. In one embodiment, the mesh comprises a semirigid bioabsorbable knit material defining two inseparable layers. Each of the layers defines interstices with an interstice of one layer communicating with a plurality of only partially aligned interstices of the other layer. The material may be knit in a rice point stitch. In another embodiment the mesh is a perforated membrane formed of a thin semirigid bioabsorbable non-knit material defining a plurality of apertures therethrough. Preferably the apertures are wider adjacent the membrane surface to contact the organ and narrower adjacent the membrane surface to be spaced from the organ, for example, generally truncated cones. Each of the apertures may define teeth projecting inwardly toward the longitudinal axis of the aperture and also toward the membrane surface to be spaced from the organ. The membrane surface to contact the organ may define protuberances disposed about the apertures and adapted to penetrate hard tissue of an organ.

BRIEF DESCRIPTION OF THE DRAWING

The above brief description, as well as further objects and features of the present invention, will be more fully understood by reference to the following detailed description of the presently preferred, albeit illustrative embodiments of the present invention, when taken in conjunction with the accompanying drawing wherein:

FIG. 1 is a fragmentary exploded front elevation view, partially in section, of the mesh and sac about to be applied in turn to a spleen, with a circled fragment of the sack being shown in a greatly enlarged view;

DETAILED DESCRIPTION OF THE PREFERRED EMBODIMENTS

Figure 2:
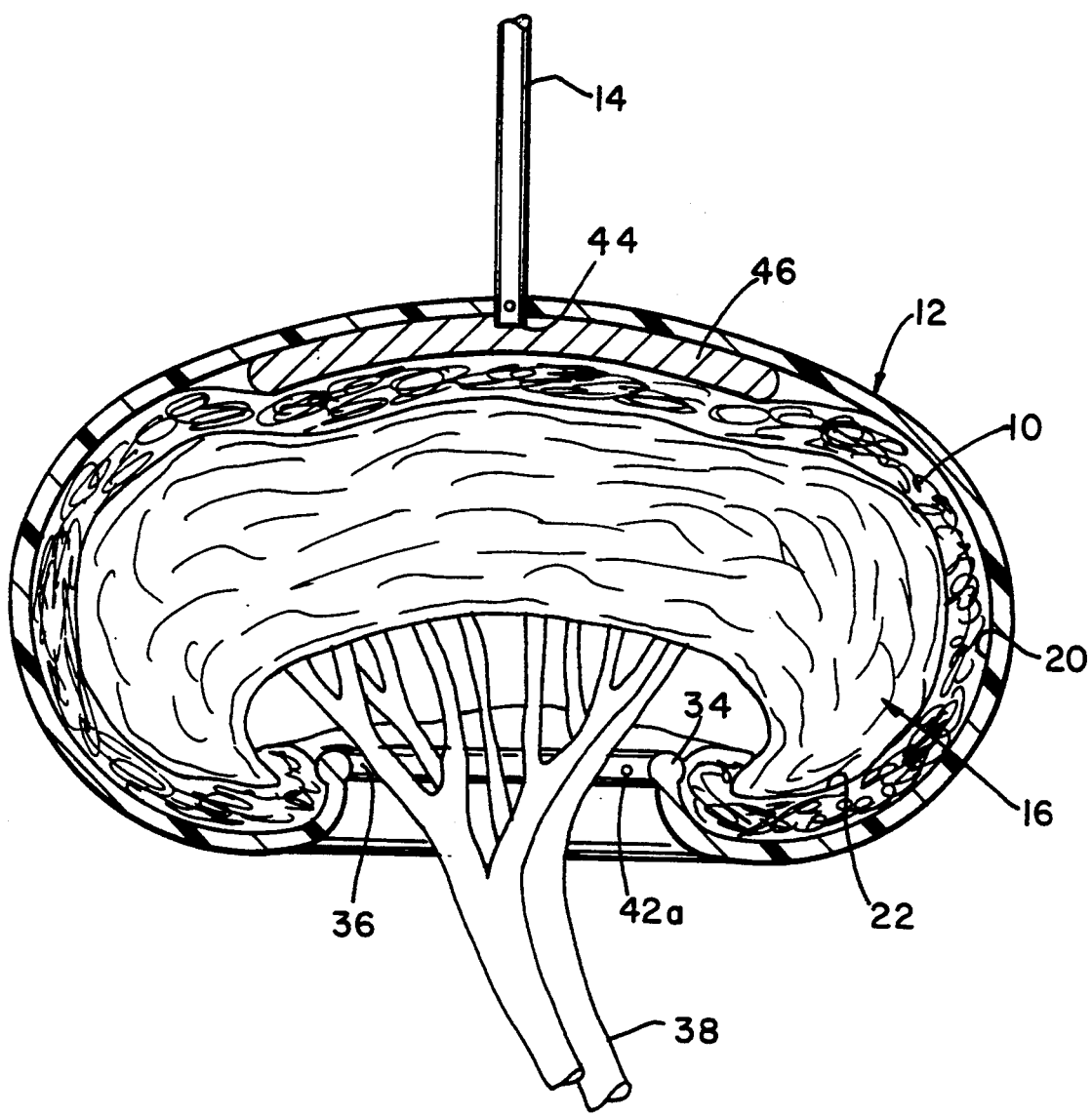
FIG. 2 is a fragmentary front elevation view, partially in section, of the mesh and sac applied to the spleen.

Referring now to FIGS. 1 and 2, therein illustrated is a first embodiment of the present invention comprising two separate elements: a bioabsorbable mesh generally designated by the reference numeral 10, and an elastic sack generally designated 12. The device is adapted to be used in conjunction with a catheter 14 and a suction device (not shown) to effect hemostasis of an organ generally designated 16, such as the spleen. It is contemplated that the mesh 10 and sack 12 will be sold together as a unit, optionally with the catheter 14. Typically the operating room where the device will be employed will have its own suction device available, but, if desired, particular kits may also include an appropriate suction device.

According to the first embodiment of the present invention, the mesh 10 is placed over the bleeding surface of the organ 16, and preferably over the entire outer surface of the organ to encapsulate the same, as illustrated in FIG. 2, and then the sack 12 is placed over the mesh 10 and over the entire outer surface of the organ 16 or portion thereof to substantially encapsulate the same. The catheter 14 provides fluid communication between the inner surface 20 of the sack 12 and the vacuum source disposed externally of the patient's body. The negative pressure between the sack 12 and the organ tissue 16, applied through the mesh 10, promotes incorporation or embedding of the mesh 10 within the organ tissue 16 by drawing portions of the organ tissue 16 through the interstices of the mesh 10. The infiltrating portions emerging from the mesh 10 increase in volume by edema, thereby maintaining the mesh 10 in place. Initially, the application of negative pressure between the inner surface 20 of the sack 12 and the outer surface 22 of the organ tissue 16 (through the mesh) leads to collapse of the blood vessels in the bleeding surface. The incorporation of the organ tissue 16 within the mesh 10 tends to keep the collapsed blood vessels of the tissue 16 in the collapsed condition.

Figure 3:
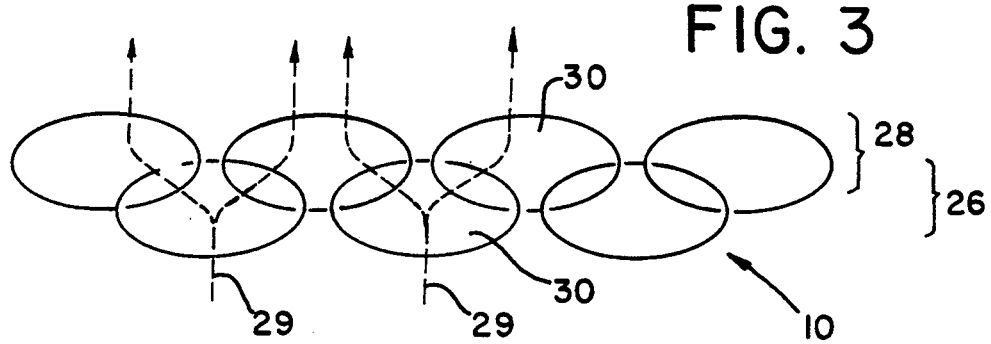
FIG. 3 is a fragmentary schematic vertical sectional view of the mesh to a greatly enlarged scale.
Figure 4:
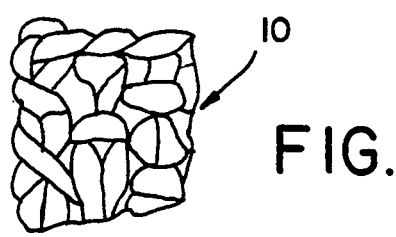
FIG. 4 is a fragmentary top plan view of the mesh.

Referring now to FIGS. 3 and 4, therein illustrated is a preferred embodiment of the bioabsorbable mesh 10 of the present invention. The mesh is preferably knit in a "rice point" stitch which provides inseparable double layers 26, 28 of mesh, although a conventional plain "left and right" stitch may be used instead. The "rice point" stitch is also known as a "moss" or "seed" stitch (see M. Dreiblatt, "Knitting for Everyone" (Doubleday & Co., Inc., Garden City, N.Y. 1964)). The resultant mesh is semirigid and substantially non-stretchable. The stitches are very dense, each of the interstices of the "rice point" mesh being approximately 1–9 mm², so that the mesh contains about 50–70 stitches per cm³. Each square centimeter of the "rice point" mesh requires from about 15 to about 60 cms of thread, preferably about 30 cms of thread. Each interstice or opening 30 of the "rice point" mesh is joined with at least four other interstices 30 (only two of the four being visible in the vertical section of FIG. 3) to provide a three-dimensional structure having interstices which remains fairly constant in size and resist in all dimensions either collapse or enlargement due to traction, suction, pressure or stretching. On the other hand, the mesh is sufficiently flexible so that it is easily conformed to the surface of an organ by the finger pressure of the surgeon or, as will be explained hereinafter, the pressure exerted by a surrounding elastic sack 12. The semirigid nature of the mesh renders it sufficiently rigid to preclude deformation under the vacuum created by the vacuum source, as described hereinafter, but sufficiently flexible to be substantially conformed over the bleeding surface of the organ 16 by the sack 12, as also described hereinafter.

A portion or finger 29 of the bleeding surface of the organ 16 infiltrating the interstices of the "rice point" mesh 10 (represented in FIG. 3 by an arrow) will, after an initial outward extension through an interstice 30 of the first or inner layer 26 thereof, be diverted at an angle to the thickness of the mesh into one of the four communicating adjoining interstices 30 of the second or outer layer 28 which are at least partially laterally displaced from the originally infiltrated interstice 30 of the first layer 26. In the adjoining interstice 30 of the second layer 28, the finger 29 will be joined by other organ portions or fingers 29 which have infiltrated originally a different interstice 30 of the first layer 26 and then been diverted to the same interstice 30 of the second layer 28. The close juxtaposition of the plurality of fingers 29 within a single interstice of the second layer 28 (each such finger 29 having initially infiltrated a different interstice 30 of the first layer 26) will promote their joinder and thus healing of the organ 16.

In addition to its primary effect of promoting hemostasis of the organ, as described above, the mesh 10 of the present invention may serve two additional functions because it is preferably disposed over the entire or substantially the entire portion of the organ 16 which will be covered by the sack 12, rather than merely the bleeding surface of the organ. First, the mesh 10 acts as a double-faced friction layer which, positioned intermediate the sack 12 and the organ 16, enables the inner surface 20 of the sack 12 to be more securely retained on the otherwise very slippery, blood-moistened outer surface 22 of the organ 16. The mesh 10 becomes embedded and fixed in the organ 16, and in turn provides a secure surface for the sack 12 to grab frictionally. Second, once the elastic sack 12 has compacted or reduced the size of the organ 16 (through its inwardly directed pressure and the resultant back force on the flow of blood into the organ) and been removed from the organ 16, the mesh 10 embedded in the organ 16 acts then to maintain the organ in its compacted size and configuration. These features are obtainable only where the organ portions 29 infiltrating the mesh 10 becomes securely locked therein, the same occurring to a lesser extent with a conventional mesh and to a much greater extent with a preferred mesh 10 according to the present invention (for example, that made by the rice point weave or another weave affording the same characteristics) where the change of direction of the infiltrating portion 29 tends to lock it within the mesh. These features are not totally obtainable with the conventional woven mesh which tends to overly soften and become too stretchable in the environment of the bleeding organ, and are fully obtained only with the more resistant, non-stretchable, semirigid preferred mesh of the present invention.

As the primary purpose of the sack 12 is to create a positive inward pressure on the outer surface 22 of the organ 16 so as to constrict and reduce the size of the organ 16 and thereby create a back pressure which will lower or terminate the subsequent flow of blood into the organ, the sack is constructed of an elastic material. The sack may be of uniform elasticity throughout or may have different levels of elasticity at different portions. For example, where the sack is to cover a spleen, the stretchability of the sack may be low at the area intended to cover the top of the spleen, but should be higher at the open end and at the portions which must be stretched to extend over the bulging sides of the spleen. Similarly, the force generated by the material tending to return it to its original configuration and dimensions is ideally greatest immediately about the aperture thereof so that the material about the aperture forms an effective air-tight seal with the organ. Preferably the sack has a lip or rolled edge 34 about its open end 36 both to reenforce the open end 36 (which typically receives the maximum stretching) and to ensure formation of an operative air-tight seal between the edge of the sack open end 36 and the organ 16 (see FIG. 2). The most desirable pressure for the sack 12 to exert on an organ 16 or portion thereof will be a function of that particular organ, and possibly even the portion thereof. For example, the pressure of the blood within the spleen is typically about 120 mm Hg. Thus, in order to substantially reduce or terminate blood flow into the spleen, the sack should exert a back pressure of about 80 to 130 mm Hg. Such a pressure on the spleen typically results in a reduction in the volume of the spleen of about 5–45%, frequently about 30%.

The sack may be fabricated in a variety of different configurations so as to be suited for particular organs and, even more specifically, for particular parts of particular organs. For example, a sack intended to completely encapsulate a spleen 16 (except for the stem 38 containing the veins and arteries leading into and out of the spleen) may have the configuration of a hollow ellipsoid so as to enable it to completely cover the spleen 16 (except for the stem 38). On the other hand, a sack intended to encapsulate a lode of the liver or a finger may have the configuration of a hollow cylinder, closed at one end and open at the other end. One skilled in the medical arts can easily determine the appropriate sack configurations for other organs or organ portions. Similarly, one skilled in the medical arts can easily determine how much of a particular organ or portion thereof must be covered or encapsulated if the sack is to remain in place on the same, notwithstanding the elastic nature of the sack and the possibly slippery nature and arcuated or irregular configuration of the organ or portion thereof. The dimensions of the sack must, of course, also be adapted to the particular organ or portions thereof to be encapsulated.

Generally the sack effectively reduces the size of the organ and creates a back pressure to diminish or terminate blood flow within a period of seconds after it is applied about the organ. Preferably the application of suction or negative pressure within the sack is delayed until after the period of time required for blood flow equilibrium to be achieved.

Furthermore, the sack 12 forces the mesh 10 to conform generally, and in most instances very closely, to the outer surface of the organ 16 in general and against any bleeding surface on the outer surface 22 of the organ in particular. This minimizes the time which a surgeon must take in order to carefully conform the mesh over the bleeding surface, or over the organ as a whole, and manually maintain it there until he begins suction.

A further advantage of the sack 12 is that it tends to force the organ portions or fingers 29, which have infiltrated the mesh 10 from the inner surface thereof and which extend outwardly from the outer surface thereof, into contact with adjacent portions 29, thereby promoting embedding of the mesh 10 within the organ 16 and joinder of the organ portions 29 on the outer surface of the mesh so as to promote healing of the organ.

The present invention contemplates two different types of sacks 12, one being bioabsorbable (like the mesh 10) and the other being non-bioabsorbable. Within these constraints the sack 12 may be formed of any material, whether natural or synthetic (such as rubber, plastic, or the like), which provides the desired elasticity and is biologically acceptable for use on the particular organ.

Where the sack 12 is made of non-bioabsorbable material, it must be removed from the interior of the body prior to closing of the incision. Nonetheless, in addition to performing the functions of reducing the blood flow to the organ and conforming the mesh to the outer surface of the organ, the non-bioabsorbable sack provides a convenient means for applying the suction or negative pressure to the bleeding surface. Thus the surgeon or his assistants need not manually maintain a suction or negative pressure device positioned over the mesh until hemorrhaging is terminated, but are free to devote themselves to seeing to the other injuries which may be present in the surrounding areas and equally demanding of urgent attention. Further, with the exception of the small tube or catheter 14 which connects the sack to the suction device, the general region about the organ is accessible to the surgeon and not blocked either by the hands or devices otherwise required to maintain a suction cup in position over the mesh.

Because a sack 12 promotes embedding of the mesh 10 within the organ 16, even after the non-bioabsorbable sack 12 is removed from the organ, the mesh 10 tends to retain the organ 16 in its diminished size, thereby effecting a continued restriction of the blood supply and lessening the chance of a recurrence of bleeding.

The sack 12 is preferably made of bioabsorbable material because the sack then, in addition to performing all of the functions noted above with respect to the non-bioabsorbable sack, affords the surgeon a greater range of options in treatment of the patient. At a minimum, the surgeon does not have to take the time required to carefully remove the sack 12 from the organ 16 without disturbing the mesh 10. More importantly, the sack 12, until it is bioabsorbed, continues support and reinforce the bioabsorbable mesh 10 which, depending upon the materials from which it is made and the size of its individual threads or filaments, may otherwise rapidly loose its mechanical strength once it is placed in the warm moist environment of an organ. Indeed, all the surgeon must do prior to closing of the incision is to remove the catheter 14 or other means connecting the suction device to the inner surface 20 of the sack 12. In fact, as discussed hereinafter in connection with the preferred embodiment of FIGS. 5 and 6, the incision may be closed about the catheter 14 so that it is not even necessary to remove the catheter 14 connecting the vacuum source and the sack 12 until long after the operation is completed.

Any conveniently available suction device capable of providing the necessary negative pressure may be employed in connection with the sack. A preferred suction device is an aspirator which enables the blood removed from the bleeding surface of the organ to be collected for immediate or delayed return to the patient.

A catheter or other flexible, hollow, air-tight tube 14 effects fluid communication between the vacuum source disposed outside the patient's body and the inner surface 20 of the sack 12 within the patient's body. Preferably the suction device, the catheter, or the sack is provided with a pressure regulating valve (not shown) to limit any unexpected surge in negative pressure and enable the surgeon to commence the negative pressure and adjust it to the desired level.

The suction or negative pressure applied to the inner surface 20 of the sack 12 should be sufficiently high that it effects the desired embedding of the mesh 10 within the organ 16 (i.e., causes infiltration of the interstices 30 of the mesh by the organ finger portions 29, especially the organ finger portions of the bleeding surface), but not so high as to cause injury to the uninjured outer surface tissue of the organ. The appropriate pressure to be applied will be a function of the type of organ, the type and extent of the wound, and the like. For example, for the spleen, a negative pressure of about 25 to about 30 mm Hg is preferred, although in particular instances lower or higher negative pressures may be usable. The negative pressure is applied until hemostasis is achieved. While typically tamponade of the bleeding parenchyma of the spleen is achieved within ten minutes, in particular instances much greater periods of time (and even several hours) may be required.

Depending upon the characteristics of the organ being treated, the organ 16 may effect unintended seals with the sack 12 (i.e., other than at the open end 36 of the sack) which have the effect of leaving portions of the organ under the sack insulated from the applied negative pressure. This potential problem may be dealt with in a number of different ways. First, the inner surface 20 of the sack may be provided with grooves 40, especially with fine grooves, in a regular or irregular pattern to resist infiltration of the grooves 40 by the organ 16, to communicate the negative pressure over the entire inner surface 20 of the sack, and thus to equalize the lower pressure around the organ. Second, a plurality of catheters 14 may be used, each connecting the vacuum source (or plurality of different vacuum sources) to different portions of the inner surface 20 of the sack so that, even if the different portions of the inner surface are not in fluid communication with one another, each is nonetheless subjected to the same negative pressure (or to different negative pressures where different air sources are employed to provide different pressures to different portions of the organ). Third, the sack itself may define therewithin or thereon a network of fluid communication lines or capillaries 42 which transmit the negative pressure from a central point contacted by the catheter 14 to the more remote regions of the inner surface 20 of the sack. In this instance the sidewall portion of the catheter 14 passing through sack 12 will define perforations communicating with the capillaries 42. Preferably one of the capillaries 42 extends to the open end 36 of sack 12 and therethrough at 42a to assist, by vacuum action, in drawing together the open sack end 36 and organ 16 to effect the desired pneumatic seal therebetween. Obviously, combinations of these techniques may also be used.

In order to prevent the sack-penetrating end 44 of the catheter 14 from becoming clogged by the sack 12 itself, preferably either the sack 12 is itself slightly rigid about the intersection of the catheter 14 and the sack 12 or a stiffening collar 46, substantially more rigid than the body of the sack 12, is disposed about the sack-penetrating end 44 of the catheter 14 to distance the more flexible material of the body of the sack 12 from the catheter end 44. The collar 46 has an opening (not shown) aligned with the catheter 14 to provide effective communication between the catheter 14 and the organ outer surface 22 via the collar 46 and mesh 10. The collar 46 may further be used to secure the catheter end 44 to the sack 12.

To use the first embodiment, the mesh 10 is applied over the bleeding surface of organ 16, and preferably also over the entire organ outer surface 22. Then the sack 12, connected by catheter 14 to a vacuum source, is stretched around the mesh and around the organ 16. Thereafter suction or negative pressure is applied via catheter 14 until hemostasis is achieved. After hemostatis is achieved, the sack 12, if non-bioabsorbable, is removed with catheter 14 and the incision closed or, if bioabsorbable, is separated from the catheter 14 which is then removed and the incision closed.

Where the bleeding surface is not on the outer surface of the organ but rather, for example, within a deep cut within the organ, in addition to the mesh on the outer surface of the organ an additional section of mesh may be manually inserted within the deep incision and adjacent the bleeding surface.

As noted above, where the sack 12 is bioabsorbable, both it and the mesh 10 may be left in place within the patient's body upon completion of the operation, with the catheter 14 merely being removed from the sack 12 prior to closing of the incision. Where the catheter 14 is itself made of a bioabsorbable material, the portion of the catheter protruding from the outer surface of the sack 12 may simply be cut away, leaving whatever portion of the catheter open end 44 is within or below the sack 12 to be bioabsorbed over time with the mesh 10 and sack 12.

Figure 6:
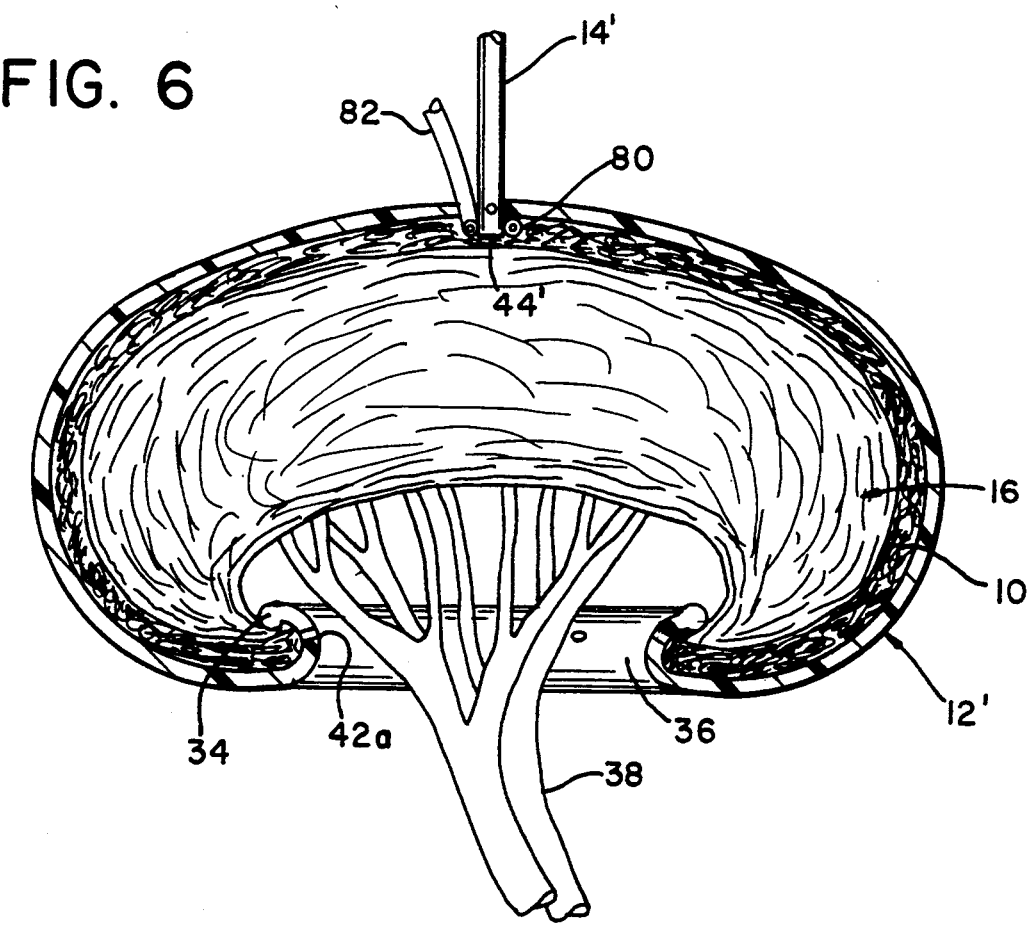
FIG. 6 is a fragmentary front elevation view, partially in section, of the unitary sac/mesh applied to the spleen.
Figure 5:
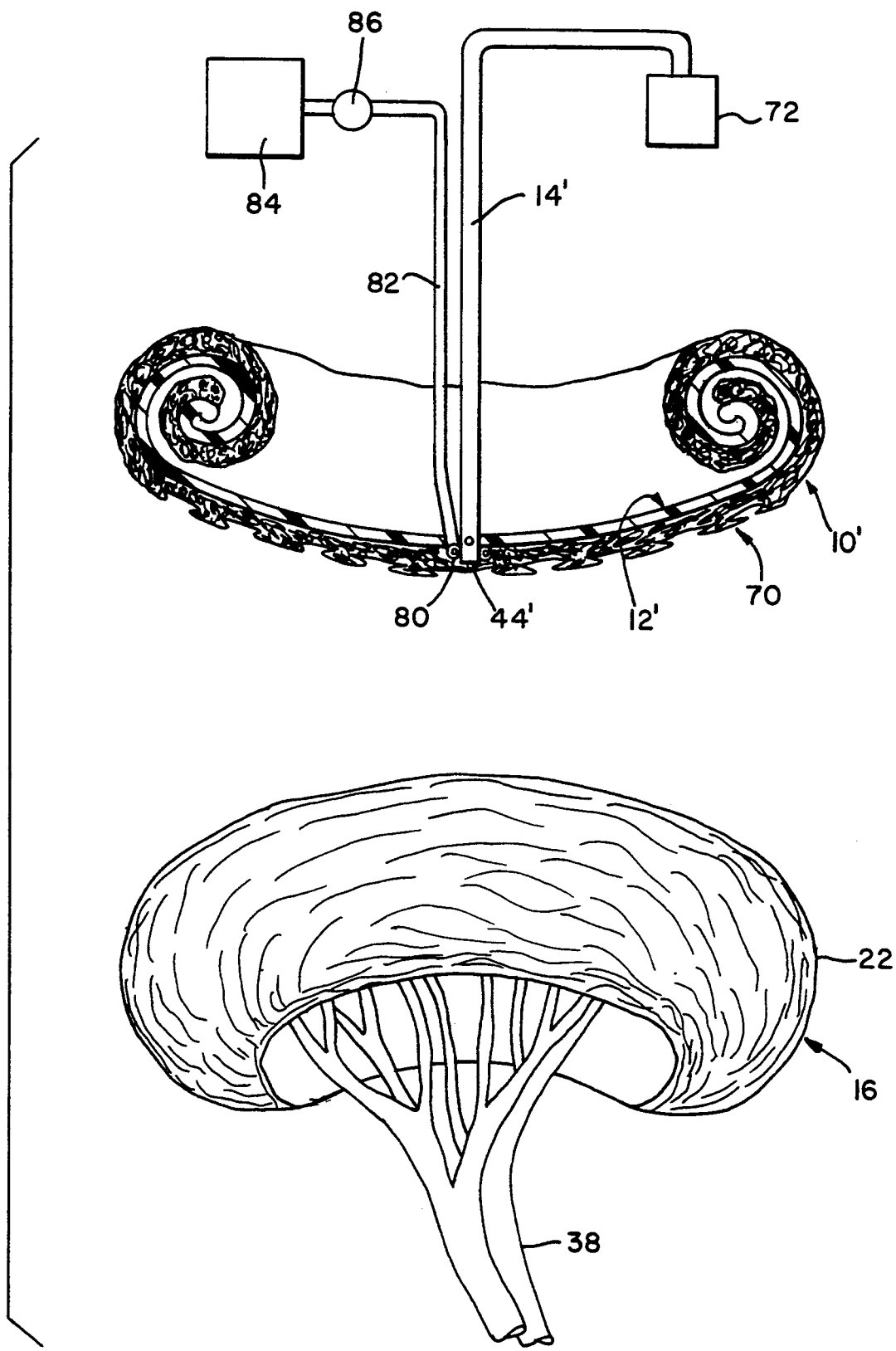
FIG. 5 is a front elevation view, partially in section, of a preferred embodiment having a unitary mesh and sac about to be applied to a fragmentarily illustrated spleen.

Referring now to FIGS. 5 and 6, therein illustrated is a second embodiment to the present invention, generally designated by the reference numeral 70, which differs from the first embodiment in two major respects. First, instead of a separate mesh 10 and sack 12, there is a bioabsorbable composite mesh/sack, applied as a unit to the organ and optionally left in the patient after the incision is substantially closed. Second, the composite mesh/sack is intended to be left in the patient's body with negative pressure or vacuum still being applied to the organ until hemostasis is achieved. As noted above, in certain instances bleeding does not terminate rapidly and may in fact continue for hours, either continuously or sporadically. In these instances, there are clear advantages to a device which may be left in operating mode even after the incision is substantially closed about the catheter which connects the interior of the mesh/sack composite to the vacuum or negative pressure source.

Elements of the second embodiment which are structurally identical to elements of the first embodiment are identified by the corresponding numerals, and those elements which are only functionally similar are identified by the corresponding numerals primed. Thus the mesh/sack composite 70 is comprised of an inner mesh layer 10', an outer sack layer 12' and connected by a catheter 14' to a vacuum or negative pressure source 72 such as an aspirator. The mesh 10' and sack 12' are both bioabsorbable and substantially coextensive. Together they form composite structure 70 having the sack 12' as the outer layer and the mesh 10' as the inner layer. A stiffening collar (not shown) may form an intermediate non-coextensive layer positioned about the catheter end. This second embodiment enables the mesh and sack elements to be applied in a single motion over the organ 16, thus facilitating and accelerating application of the device by the surgeon relative to the time and effort required to sequentially position first the mesh 10, and then the sack 12. Of course, where the bleeding surface is disposed within the organ 16 rather than on its outer surface 22, additional pieces of mesh 10 may be applied to the bleeding surface as required.

In composite 70, the inner mesh layer 10' is secured to the outer mesh layer 12° only at points with excess material of inner mesh layer 10' being provided between the points before the composite is used. Thus, when the composite is used by stretching it over an organ 16, the excess material of inner mesh layer 10' enables the outer sack layer 12' to expand as necessary to fit over the organ 16. Alternatively, although less desirably, the mesh forming the inner layer 10' of the composite 70 may be more stretchable than standard mesh 10 and secured to the outer sack layer 12' uniformly at the interface between the two layers 10', 12', with the resultant composite 70 being able to stretch as necessary over the organ.

In order to enable the catheter 14' to be removed from the mesh/sack composite 70 once hemostatis is obtained, so that the incision may be fully closed, the catheter end 44' is provided with a surrounding elastic inflation collar 80 which is inflatable either pneumatically or hydraulically by means of an inflation catheter 82 connecting the inflation collar 80 to an inflation source 84 through a valve 86 disposed outside of the patient's body. Preferably the inflation collar 80 is a small inflatable elastic balloon affixed to the end of the vacuum catheter 14' and is hydraulically inflatable, and the inflation source 84 is a reservoir, optionally pressurized, for saline solution or like bioacceptable liquid for inflating the collar 80. While the inflation catheter 82 connected to inflation source 84 is shown separately from the vacuum catheter 14' connected to the vacuum or negative pressure source 72, clearly one tube 82, 14' may be inserted coaxially within the other tube 14', 82 for at least the lengths of the tubes within the patient's body. While the inflation collar 80 is shown as being disposed intermediate the inner surface of the outer sack layer 12' and the outer surface of the inner mesh layer 10', if desired either layer 10', 12' or the optional stiffening collar could be provided with appropriate recesses (not shown) to receive the inflated inflation collar 80 and maintain it in position as long as it is inflated.

When the inflation collar 80 is inflated by the inflation liquid from inflation source 84 via inflation catheter 82, it enters into an appropriate recess to releasably secure catheter end 44' to the composite 70 and preclude its withdrawal. During the operation the inflation collar 80 is maintained in its inflated state by closing of the valve 86 and thus closing of the inflation tube 82. After the operation is completed and the incision is closed about the tubes 82, 14', suction or negative pressure continues to be applied to the composite 70 from the negative pressure or vacuum source 72 via catheter 14' either continuously or intermittently as needed (for example, whenever bleeding resumes as evidenced by the appearance of blood in the aspirator 72), when permanent hemostasis is achieved, it is only necessary to open the valve 86 from outside the patient's body, at which point the stretched outer sack layer 12' will force the inflation liquid from inflation collar 80 back out through inflation catheter 82 and valve 86 into the inflation source 84, thereby allowing the inflation collar 80 to collapse. Once the inflation collar 80 is collapsed, both tubes 82 and 14' are then easily withdrawn from the composite 70 and removed from the patient's body, whereby the surgeon has only to complete closure of the incision.

Prior to use the composite 70 may be compactly and conveniently rolled up, as illustrated in FIG. 5, in the manner of a condom ready to be applied to the organ.

It will be appreciated that the composite mesh/sack construction 70 may be employed with a non-releasable catheter 14 (as in the first embodiment) which is not releasable from the composite 70 from outside the patient's body where it is intended that the catheter will be removed at the conclusion of the operation.

To use the second embodiment, the center point of the composite 70 is applied to the organ 16 and the rolled up edges are unrolled and stretched around the organ outer surface 22 as a unit. Suction or negative pressure is applied intermediate the sack outer layer 12' and the organ outer surface 22. The catheter 14' may be in place during application of the composite 70 on the organ 16 or may be inserted after the composite 70 is in place. In either case, once the catheter 14' is appropriately positioned with its inflation collar 80 adjacent an appropriate recess of the composite 70, valve 86 is opened to permit the inflation source 84 to inflate the collar 80 via inflation catheter 82, after which the valve 86 is closed. The incision may then be closed about the catheters 14', 82 with negative pressure still being applied to catheter 14'. When hemostasis is achieved, valve 86 may be opened, thereby permitting collapse of the inflation collar 80 and thus withdrawal of the suction catheter 14' (including inflation collar 80) and inflation catheter 82 from the composite 70. Only the relatively small portion of the incision left open for passage of the catheters 82, 14' need then be sutured.

Figure 7:
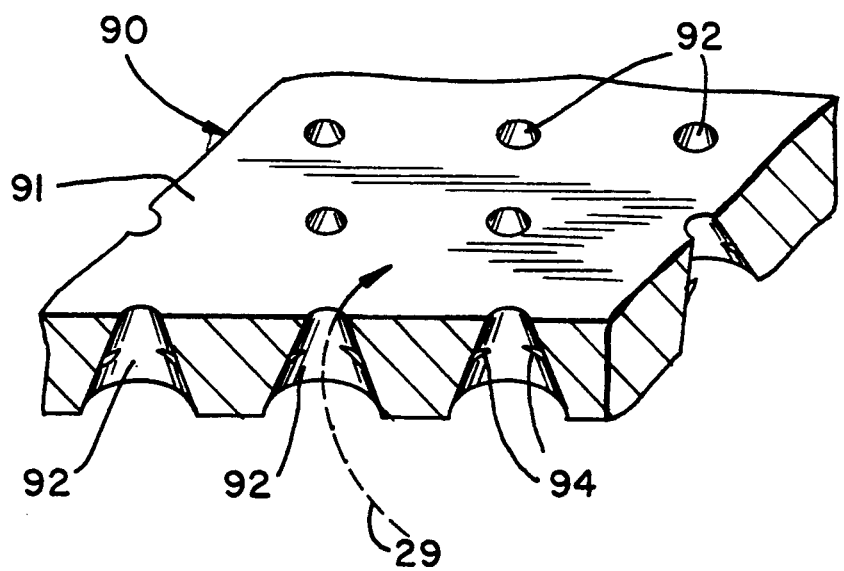
FIG. 7 is a fragmentary isometric view, partially in section, showing the upper surface of an alternative mesh.

The term "mesh" is employed in its broad sense of something that snares or entraps. While the mesh 10, 10' described hereinabove is preferably a knit material, and more particularly a material which has been knitted in a "rice point" stitch, non-knitted materials may be used in the present invention as well. For example, referring now to FIG. 7, a perforated non-knit membrane 90 may also be used as the mesh 10, 10'. The membrane 90 comprises a thin bioabsorbable semirigid material 91 (about 3–7 mm thick) defining a plurality of apertures 92 extending therethrough. While the apertures 92 may be cylindrical in configuration, they are preferably generally conical, with the inner surface of the mesh adapted to contact the organ being the broader base (about 3–6 trim in diameter) and the truncated tip or top of the cone (about 1–3 mm in diameter) being the outer surface of the mesh adapted to contact the sack. A preferred separation between adjacent conical bases is about 1–4 mm so that there are about 1–6 apertures per $cm^2$.

Each aperture 92—whether or not conical in configuration—preferably defines one or more teeth 94 which extend inwardly towards the longitudinal axis of the aperture 92 to engage any organ portions or fingers 29 (represented by phantom arrows in FIG. 7) which enter into the aperture 92. There may be a plurality of rows of teeth 94, and the teeth 94 may abut adjacent teeth 94 to form a continuous ring or inward projection of the aperture 92. The teeth 94 may extend perpendicular to the longitudinal axis of the aperture 92, but preferably extend at an upward angle thereto (toward the organ-contacting end of the axis) to facilitate entry of the organ fingers 29 thereinto and by engagement therewith enhance retention of the organ fingers 29 within the aperture 92.

In instances where the injury is rather deep and not merely a surface injury, the mesh may desirably be formed by two or more of the perforated membranes 90 disposed one on top of the other (preferably with a slight separation of about 3 mm therebetween) or a single perforated membrane of more than the usual thickness and defining two or more at least partially longitudinally aligned and communicating half-apertures 92, each having optionally its own unique shape and teeth.

The mesh of membrane 90 is utilized in the same member as the mesh 10, 10' with two additional advantages. First, the drawing of the tissue fingers 29 through the conical apertures 92 from the broad base through the truncated top causes the tissue fingers 29 to initially decrease in volume (and thereby further collapse the blood vessels therein) and then expand as a result of edema as they emerge from the aperture 92. Second, the teeth 94 trap the tissue fingers 29, thereby preventing a retreat thereof and insuring secure imbedding of the membrane 90 within the organ 16. Neither of these beneficial effects are obtained in the knit mesh 10, 10' where the interstices are cylindrical and devoid of teeth.

Figure 8:
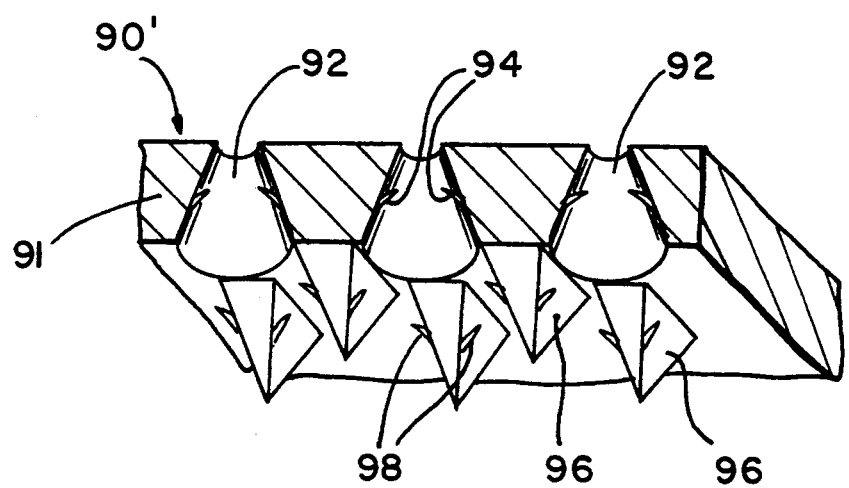
FIG. 8 is a fragmentary isometric view, partially in section, showing the lower surface of a variation of the alternative mesh.

Referring now to FIG. 8, where the membrane 90 will be employed for effecting hemostasis in hard tissue (such as kidney and muscle tissue) as opposed to soft tissue (such as liver and spleen tissue), the organ-contacting surface of the membrane 90 may be provided with protuberances 96 adapted to facilitate penetration of the hard tissue of the organ 16 and thereby promote embedding of the mesh 90 within the tissue. The protuberances 96 are preferably pyramidic in shape with the points pointing in the direction of the organ 16 so that, as the membrane 90 is placed over the organ 16, the points of the pyramids 96 penetrate the hard tissue of the organ 16. The protuberances may be 2–8 mm in height with each side of the base being about 1–4 mm. If desired, teeth 98 may also be provided on the protuberances to further facilitate engagement of the tissue by the protuberances 96, the teeth 98 extending outwardly from the protuberances and preferably towards the base thereof. The protuberances 96 are preferably disposed about the periphery of the broad base of the conical apertures 92 in such a manner as to not interfere with the communication of suction through the apertures 92. For example, each broad base of a conical aperture 92 may be surrounded by the bases of four pyramids 96.

Clearly the preferred meshes 10, 90 of the present invention, while intended for use in connection with the sack 12 of the present invention (whether the sack 12 is a separate element or a composite therewith), will also find utility in conventional suction techniques for effecting hemostasis, such as the aforementioned techniques expounded by Dr. Aglietti which did not utilize a sack.

Any reference herein to the sack or mesh covering or encapsulating an organ, as used herein, does not imply 100% encapsulation of the organ, but rather allows for interruption of the sack or mesh for a stem or similar portion containing veins and arteries connecting the organ to other portions of the body.

Now that the preferred embodiments of the present invention have been shown and described in detail, various modifications and improvements thereon will become readily apparent to those skilled in the art. Accordingly, the appended claims should be construed broadly, and in a manner consistent with the spirit and scope of the invention herein.

I claim:

1. Knit mesh for use in effecting hemostasis of an organ comprising a mesh of semirigid bioabsorbable knit material defining two layers inseparably knit together, each of said layers defining interstices with an interstice of one layer communicating with a plurality of only partially aligned interstices of the other layer.

2. Knit mesh for use in effecting hemostasis of an organ comprising a mesh of semirigid bioabsorbable knit material defining two inseparable layers, each of said layers defining interstices with an interstice of one layer communicating with a plurality of only partially aligned interstices of the other layer, the material being knit in a rice point stitch.

3. Non-knit mesh for use in effecting hemostasis of an organ comprising a perforated membrane formed of a thin semirigid bioabsorbable, biocompatible non-knit material defining a plurality of truncated, generally conical and spaced apertures wherein the membrane is adapted to at least partially surround the organ.

4. The apparatus of claim 3 wherein the membrane surface to contact the organ defines protuberances disposed about each of said apertures and adapted to penetrate hard tissue of an organ.

5. The apparatus of claim 3 wherein said apertures are wider adjacent the membrane surface to contact the organ and narrower adjacent the membrane surface to be spaced from the organ.

6. The apparatus of claim 5 wherein said apertures are generally truncated cones.

7. Non-knit mesh for use in effecting hemostasis of an organ comprising a perforated membrane formed of a thin semirigid bioabsorbable non-knit material defining a plurality of apertures therethrough, said apertures being wider adjacent the membrane surface to contact the organ and narrower adjacent the membrane surface to be spaced from the organ, each of said apertures defining teeth projecting inwardly toward the longitudinal axis of said aperture and also toward said membrane surface to be spaced from the organ.

8. A device for effecting hemostasis of an organ comprising:
(A) an air-permeable mesh of semirigid bioabsorbable material defining interstices and adapted to be generally conformingly disposed on at least the bleeding surface of an organ; and
(B) a sack defining a continuous surface made of flexible, elastic, resilient air-impermeable material and an opening at one portion thereof adapted to enable passage of the bleeding surface of the organ therethrough, said elastic material being configured and dimensioned to be elastically stretched over said mesh and over a substantial portion of the organ and upon release to compress the organ portion and thereby decrease the flow of blood thereto; said sack further including means for the operative attachment of the undersurface thereof to a vacuum source so that portions of the organ may be pulled outwardly by the vacuum into the interstices of said underlying mesh to promote hemostasis;
said mesh being a knit material defining two inseparable layers, each of said layers defining interstices with an interstice of one layer communicating with a plurality of only partially aligned interstices of the other layer.

9. The device of claim 8 wherein said knit material is knit in a rice point stitch.

10. A device for effecting hemostasis of an organ comprising:
(A) an air-permeable mesh of semirigid bioabsorbable material defining interstices and adapted to be generally conformingly disposed on at least the bleeding surface of an organ; and
(B) a sack defining a continuous surface made of flexible, elastic, resilient air-impermeable material and an opening at one portion thereof adapted to enable passage of the bleeding surface of the organ therethrough, said elastic material being configured and dimensioned to be elastically stretched over said mesh and over a substantial portion of the organ and upon release to compress the organ portion and thereby decrease the flow of blood thereto; said sack further including means for the operative attachment of the undersurface thereof to a vacuum source so that portions of the organ may be pulled outwardly by the vacuum into the interstices of said underlying mesh to promote hemostasis;
said mesh being a perforated membrane formed of a thin non-knit material defining a plurality of interstices defining apertures therethrough.

11. The apparatus of claim 10 wherein the membrane surface to contact the organ defines protuberances disposed about said apertures and adapted to penetrate hard tissue of an organ.

12. The apparatus of claim 10 wherein said apertures are wider adjacent the membrane surface to contact the organ and narrower adjacent the membrane surface to be spaced from the organ.

13. The apparatus of claim 12 wherein said apertures are generally truncated cones.

14. The apparatus of claim 12 wherein each of said apertures defines teeth projecting inwardly toward the longitudinal axis of said aperture and also toward said membrane surface to be spaced from the organ.

* * * * *